United States Patent
Suen et al.

(10) Patent No.: US 11,731,998 B2
(45) Date of Patent: Aug. 22, 2023

(54) METHOD OF PREPARING FERRIC CARBOXYMALTOSE

(71) Applicant: FORMOSA LABORATORIES, INC, Taoyuan (TW)

(72) Inventors: Rung-Tian Suen, Taoyuan (TW); Yao-Ting Wang, Taoyuan (TW); Keng-Ming Chang, Taoyuan (TW); Ming-Kuang Hsu, Taoyuan (TW)

(73) Assignee: FORMOSA LABORATORIES, INC, Taoyuan (TW)

( * ) Notice: Subject to any disclaimer, the term of this patent is extended or adjusted under 35 U.S.C. 154(b) by 0 days.

(21) Appl. No.: 17/579,818

(22) Filed: Jan. 20, 2022

(65) Prior Publication Data

US 2023/0052476 A1 Feb. 16, 2023

(30) Foreign Application Priority Data

Jul. 29, 2021 (TW) .................................. 110127898

(51) Int. Cl.
*C07H 3/06* (2006.01)
(52) U.S. Cl.
CPC ..................................... *C07H 3/06* (2013.01)
(58) Field of Classification Search
CPC ....................................................... C07H 3/06
See application file for complete search history.

(56) References Cited

U.S. PATENT DOCUMENTS

| 7,612,109 B2 | 11/2009 | Geisser et al. |
| 2017/0232040 A1* | 8/2017 | Tseti ...................... A61K 33/26 536/121 |
| 2021/0155651 A1 | 5/2021 | Srinivasan et al. |

FOREIGN PATENT DOCUMENTS

CN 106236707 A 12/2016

OTHER PUBLICATIONS

Dias et al., Carbohydrate Polymers, 2011, 86, p. 185-191. (Year: 2011).*
Office Action dated Feb. 7, 2022 issued by the Taiwanese Intellectual Property Office for Taiwanese Application No. 110127898.

* cited by examiner

*Primary Examiner* — Jonathan S Lau
(74) *Attorney, Agent, or Firm* — Heslin Rothenberg Farley & Mesiti P.C.

(57) ABSTRACT

Provided is a method of preparing ferric carboxymaltose with weight average molecular weight between 100,000 and 400,000. The method includes reacting an oxidized maltodextrin solid with an iron (III) salt solution in acidic and basic conditions in sequence to afford ferric carboxymaltose, wherein the oxidized maltodextrin solid has a dextrose equivalent of less than 4. The ferric carboxymaltose prepared by the method can withstand high-temperature sterilization with high stability and facilitate storage.

9 Claims, No Drawings

METHOD OF PREPARING FERRIC CARBOXYMALTOSE

TECHNICAL FIELD

The disclosure is directed to a method of preparing ferric carboxymaltose, and particularly relates to a method for improving the stability of ferric carboxymaltose while preparing the same.

BACKGROUND

Ferric carboxymaltose is an iron complex, which consists of a carbohydrate shell and an iron (III) hydroxide core. It has been clinically proven that intravenous injection of ferric carboxymaltose to patients with iron deficiency anemia (IDA) can replenish iron and rapidly increase the patient's hemoglobin level to achieve a therapeutic effect. Ferric carboxymaltose will directly enter the human body through intravenous injection so its terminal process in preparation of the ferric carboxymaltose has to include a sterilization step. Since the sterilization is carried out at 121±1° C., ferric carboxymaltose has to keep stable at high temperature.

The prior art, such as U.S. Pat. No. 7,612,109B2, utilizes maltodextrin having a dextrose equivalent (DE) of 5 to 22 to react with an aqueous hypochlorite solution to afford an aqueous solution of oxidized maltodextrin, which then directly reacts with an iron (III) salt solution to give the ferric carboxymaltose complex. However, it has been found in the art that after the formation of the complex, the reaction mixture will experience gelation and precipitation in subsequent reaction processes, and cannot stably produce ferric carboxymaltose.

In addition, if the ferric carboxymaltose produced by the prior art is further sterilized at high temperature, it has been found in experiments that there still exist unstable conditions such as sharp changes in molecular weight, which need to be further improved.

SUMMARY

The present disclosure provides a method of preparing ferric carboxymaltose with weight average molecular weight (Mw) between 100,000 and 400,000, and the method comprises reacting an oxidized maltodextrin solid with an iron (III) salt solution under acidic and basic conditions in sequence to afford the ferric carboxymaltose, wherein the oxidized maltodextrin solid has a dextrose equivalent of less than 4.

In an embodiment, the oxidized maltodextrin solid is prepared by reacting an aqueous solution containing maltodextrin having the dextrose equivalent of 8 to 15 with an oxidizing agent, and utilizing an organic solvent to precipitate the oxidized maltodextrin solid.

In an embodiment, the oxidizing agent is a combination of hypochlorite salts and bromide salts, and the maltodextrin aqueous solution and the oxidizing agent are reacted under a basic condition.

In an embodiment, the oxidizing agent is a combination of hydrogen peroxide and chlorite, and the maltodextrin aqueous solution and the oxidizing agent are reacted under an acidic condition.

In an embodiment, the organic solvent is an alcohol or a ketone, such as methanol, ethanol, propanol, isopropanol, acetone or any combination thereof.

In an embodiment, the oxidized maltodextrin solid is added to the reaction in a batch or in batches in the method of preparing the ferric carboxymaltose.

In an embodiment, the oxidized maltodextrin solid is added before reacting under the basic condition in the method of preparing the ferric carboxymaltose.

In an embodiment, the reaction under acidic and basic conditions in sequence can be achieved by adding a base in an acidic condition in the method of preparing the ferric carboxymaltose. In another embodiment, a weak base is added first, and then a strong base is added. In another embodiment, a part of the oxidized maltodextrin solid is added to the reaction after a weak base is added.

In an embodiment, the method of the present disclosure further comprises adjusting the reaction to an acid condition after reacting the oxidized maltodextrin solid under the basic condition.

In an embodiment, the method of the present disclosure further comprises purifying and isolating the prepared ferric carboxymaltose through ultrafiltration.

In an embodiment, the method of the present disclosure further comprises spray drying the prepared ferric carboxymaltose to afford the ferric carboxymaltose solid.

In an embodiment, the method of the present disclosure further comprises dissolving the ferric carboxymaltose solid in pure water to prepare a solution and sterilizing the solution.

The disclosed method of preparing ferric carboxymaltose has the following advantages:

1. The prepared ferric carboxymaltose solution (the intermediate solution, also a crude product) does not undergo precipitation or gelation while using an oxidized maltodextrin solid having the dextrose equivalent of less than 4. The purified ferric carboxymaltose solid has high stability and can be stored stably for at least several weeks. Even if the solution prepared from the purified ferric carboxymaltose solid is sterilized by high temperature, there will be no drastic change in molecular weight.
2. In the step of precipitating the oxidized maltodextrin solid with an organic solvent, recycling the organic solvent can reduce the cost and have the benefit of environmental protection.
3. Different from the prior art, which exists some problems of solvent residues and solvent wastes resulting from the need of adding a large amount of solvent to crystallize ferric carboxymaltose, the present disclosure utilizes ultrafiltration and spray drying to treat the ferric carboxymaltose solution. Hence, the prepared ferric carboxymaltose solid has the characteristics of improved purity, reduced cost, and environmental protection.

DETAILED DESCRIPTION

The implementation of the present disclosure is illustrated by the following embodiments. A person having ordinary skill in the art can easily understand the scope and effects of the present disclosure based on the contents herein. However, the embodiments described herein are not intended to limit the present disclosure, and the technical features or solutions can be combined with each other. The present disclosure can also be implemented or applied by other different implementations, and various details recited herein can also be given different changes or modifications according to different viewpoints and applications without departing from the present disclosure.

Unless otherwise specified, a part that "comprises," "includes," "contains" or "has" elements mentioned herein can further include other elements, components, structures, regions, locations, devices, systems, steps, or connection relationships and other elements instead of excluding these other elements.

Unless specifically stated otherwise herein, the singular forms "a," "an" and "the" described herein also include plural forms, and the term "or" and "and/or" described herein can be used interchangeably.

A numerical range described herein is inclusive and combinable, and any value falling within the numerical range described herein can be used as the maximum or minimum value to derive a sub-range. For example, the numerical range of "dextrose equivalent is less than 4" should be understood as including any sub-ranges less than 4, such as less than or equal to 3.5, less than or equal to 3, less than or equal to 2.5, less than or equal to 2, less than or equal to 1.5, and less than or equal to 1. In addition, if a value falls within the ranges described herein, it shall be deemed to be included in the scope of the present disclosure. For example, "dextrose equivalent is 2" is of course included in the present disclosure, since "dextrose equivalent is 2" falls within the range of "dextrose equivalent is less than 4."

As used herein, the "dextrose equivalent" is determined with Fehling's solution.

The present disclosure provides a method of preparing ferric carboxymaltose, of which the weight average molecular weight is between 100,000 and 400,000, wherein the method comprises the following steps: reacting a maltodextrin aqueous solution with an oxidizing agent to afford oxidized maltodextrin; isolating the oxidized maltodextrin to give an oxidized maltodextrin solid, wherein the oxidized maltodextrin has a dextrose equivalent of less than 4; reacting the oxidized maltodextrin solid with an iron (III) salt solution in acidic and basic conditions in sequence to afford the ferric carboxymaltose; purifying and isolating the ferric carboxymaltose through ultrafiltration; and spray drying the ferric carboxymaltose.

In the present disclosure, conventionally or commercially available maltodextrin can be used. In an embodiment, the dextrose equivalent of the maltodextrin may be 8 to 15. In other embodiments, the dextrose equivalent of the maltodextrin may be 8 to 14.

In an embodiment of the present disclosure, the reaction temperature may be about 20° C. to 45° C. for the reaction between the maltodextrin aqueous solution and the oxidizing agent, and the reaction time may be about 0.5 to 25 hours. A combination of hypochlorite salts and bromide salts can be used as the oxidizing agent. Hypochlorite salts may be, for example, alkali metal hypochlorites, such as sodium hypochlorite and potassium hypochlorite. Bromide salts may be, for example, alkali metal bromides, such as sodium bromide and potassium bromide. The oxidation reaction, when using this kind of oxidizing agent, is under basic conditions, e.g., pH 8.5 to 12, or 9 to 11.

In another embodiment of the present disclosure, a combination of hydrogen peroxide and chlorite salts can be used as the oxidizing agent. Chlorite salts may be, for example, alkali metal chlorites, such as sodium chlorite and potassium chlorite. The oxidation reaction, when using this kind of oxidizing agent, is under acidic conditions, e.g., pH 2 to 6, or 3 to 6.

In an embodiment of the present disclosure, the step of isolating the oxidized maltodextrin can precipitate the oxidized maltodextrin solid through an organic solvent. Organic solvents may be, for example, alcohols, ketones, esters, and any combinations thereof. Exemplary examples of alcohols may be, for example, methanol, ethanol, propanol, and isopropanol. Exemplary examples of ketones may be, for example, acetone. In addition, the organic solvent can also be recycled and reused, which reduces costs and is environmentally friendly.

The oxidized maltodextrin solid used in the present disclosure has the dextrose equivalent of less than 4, less than 3, less than 2, or less than 1, such as 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.65, 0.6, 0.55 or 0.5, etc. The present disclosure provides the use of the oxidized maltodextrin solid having dextrose equivalent of less than 4 for making the subsequently formed ferric carboxymaltose with high stability.

In an embodiment of the present disclosure, iron citrate and iron halides, such as iron chloride, may be used as iron (III) salt.

In the present disclosure, reacting an oxidized maltodextrin solid with an iron (III) salt in an acidic reaction condition can avoid the formation of iron (III) hydroxide. Here, the acidic reaction condition can refer to, for example, an environment with pH of 4 or less, 3 or less, 2 or less, or 1 or less, which is formed by dissolving the iron (III) salt in water or adding an additional acid in the iron (III) salt solution. Then, increasing pH generates a β-FeOOH iron core which is chelated with the oxidized maltodextrin via coordinate bonds and hydrogen bonds.

In an embodiment, the step of increasing pH can be achieved by adding a conventional base. In another embodiment, gradually increasing pH can be achieved by slowly adding a conventional weak base, e.g., increasing the pH of an acidic environment to 2 or more, 3 or more, 4 or more, or 5 or more. The time of the reaction between the oxidized maltodextrin solid and the iron (III) salt in the acidic reaction condition is about 1 to 48 hours. After the above-mentioned acidic reaction condition, it is converted to a basic reaction condition by adding a conventional strong base to increase the pH of the acidic reaction condition, e.g., raising pH to 11 or more, 12 or more, 13 or more, or 14 or more.

In an embodiment of the present disclosure, during the reaction of the oxidized maltodextrin solid and the iron (III) salt, the oxidized maltodextrin solid can be added to the reaction system totally in a batch or separately in several batches. In another embodiment, the addition of the oxidized maltodextrin solid is completed before the reaction condition turns basic. For example, it can be selected to react all the oxidized maltodextrin solid with the iron (III) salt in a strong acidic environment. Alternatively, it can be selected to react a part of the oxidized maltodextrin solid with the iron (III) salt in a strong acidic condition, subsequently to reduce the acidity of the system with a weak base, and further to add the other part of the oxidized maltodextrin solid for reaction with the iron (III) salt. After all, the reaction environment is adjusted with a strong base to become basic.

In an embodiment of the present disclosure, the reaction between the oxidized maltodextrin solid and the iron (III) salt is finally readjusted from basic to acidic to give ferric carboxymaltose. The acidity here is, for example, pH 5 to 6.

In an embodiment of the present disclosure, ultrafiltration is applied to the ferric carboxymaltose solution. It utilizes the pore size of the ultrafine membrane to screen the passing molecules/particles, thereby purifying and isolating the ferric carboxymaltose. In another embodiment, the ferric carboxymaltose solution is further spray dried to afford the ferric carboxymaltose solid without large consumption of solvent.

The weight average molecular weight of the ferric carboxymaltose prepared by the method of the present disclosure is between 100,000 and 400,000, or between 200,000 and 350,000. After high temperature sterilization of the ferric carboxymaltose solution which is prepared by dissolving the ferric carboxymaltose solid in water, the percentage change in the weight average molecular weight is 15% or less, 10% or less, 9% or less or 8% or less. Furthermore, after storage of the ferric carboxymaltose solution for 4 weeks at room temperature or 40° C., the percentage change in the weight average molecular weight is also 15% or less, 10% or less, 9% or less or 8% or less.

The present disclosure describes further details with the following preparation examples and examples, but these preparation examples and examples are by no means intended to limit the scope of the present disclosure.

Preparation Example 1: Preparation of Oxidized Maltodextrin by Sodium Hypochlorite 400 g of maltodextrin was dissolved in 1,200 mL of water with stirring at 25 to 30° C. for 45 minutes. 1.04 g of 30% sodium hydroxide aqueous solution and 2.6 g of sodium bromide were added to the previous solution at 25 to 30° C., followed by 148 g of 6% to 14% sodium hypochlorite aqueous solution at 20 to 30° C. The reaction mixture was stirred at the same temperature for 2 hours, slowly added to 5,056 g of methanol at 0 to 10° C., and stirred at the same temperature for 45 minutes. The precipitated solid was filtered out and dried to give the oxidized maltodextrin solid.

The yield of the oxidized maltodextrin solid is 362 g, and the measured value of dextrose equivalent is 1.9.

Preparation Example 2: Preparation of Oxidized Maltodextrin by Hydrogen Peroxide 240 g of maltodextrin was dissolved in 480 g of water with stirring at 20 to 30° C. for 45 minutes. Next, 72.0 mL of 0.67 M sodium dihydrogen phosphate (NaH2PO4) buffer solution was added to the previous solution at 20 to 30° C., followed by 11.2 mL of 50% hydrogen peroxide aqueous solution and 260.6 g of 7.9% sodium chlorite (NaClO2) aqueous solution at 5 to 10° C. in sequence. The reaction mixture was heated to 40 to 45° C. with stirring for 25 hours, then slowly added to 3,033 g of methanol at 0 to 10° C., and stirred at the same temperature for 45 minutes. The precipitated solid was filtered out and dried to afford the oxidized maltodextrin solid.

The yield of the oxidized maltodextrin solid is 194 g, and the measured value of dextrose equivalent is <1.

Preparation Example 3: Preparation of Oxidized Maltodextrin by Hydrogen Peroxide Referring to the method of Preparation Example 2, 360 g of maltodextrin was used to prepare oxidized maltodextrin, except the reaction mixture was heated to 40 to 45° C. with stirring for 50 minutes.

The yield of the oxidized maltodextrin solid is 293 g, and the measured value of dextrose equivalent is 2.58.

Preparation Example 4: Preparation of Oxidized Maltodextrin by Hydrogen Peroxide Referring to the method of Preparation Example 2, 360 g of maltodextrin was used to prepare oxidized maltodextrin, except the reaction mixture was heated to 40 to 45° C. with stirring for 40 minutes.

The yield of the oxidized maltodextrin solid is 292 g, and the measured value of dextrose equivalent is 2.93.

Preparation Example 5: Preparation of Oxidized Maltodextrin by Hydrogen Peroxide Referring to the method of Preparation Example 2, 240 g of maltodextrin was used to prepare oxidized maltodextrin, except the reaction mixture was heated to 35 to 40° C. with stirring for 45 minutes.

The yield of the oxidized maltodextrin solid is 188 g, and the measured value of dextrose equivalent is 3.57.

Example 1: Preparation of the Ferric Carboxymaltose Solution Using the Oxidized Maltodextrin from Preparation Example 1

5.88 g of 3 N hydrochloric acid was added to the ferric chloride solution (with the iron content of 10 g) at 25±5° C. 20 g of the oxidized maltodextrin solid prepared from Preparation Example 1 was dissolved in the ferric chloride solution at 25±5° C. with stirring for 45 minutes. Subsequently, 131.16 g of 17.3% sodium carbonate aqueous solution was added to the reaction mixture at 25±5° C. and stirred at the same temperature for more than 30 minutes.

Further, 3.65 g of the oxidized maltodextrin solid prepared from Preparation Example 1 was added to the previous solution at 25 to 30° C. The reaction mixture was stirred at the same temperature for 45 minutes, adjusted to pH 11 or more at 25±5° C. by the addition of a sodium hydroxide aqueous solution, heated to 50 to 55° C. with stirring for 1 hour, subsequently adjusted to pH 5 to 6 by the addition of hydrochloric acid, stirred at 50 to 55° C. for 70 minutes, cooled to 25 to 30° C., and purified and isolated by ultrafiltration to give an intermediate solution. GPC analysis result shows that the weight average molecular weight of the ferric carboxymaltose in the intermediate solution is 204 KDa.

The intermediate solution was condensed to the concentration of 9.74% and spray dried to afford a ferric carboxymaltose solid. Next, the ferric carboxymaltose solid was dissolved in pure water to give a 17% ferric carboxymaltose solution which was subsequently sterilized at 121±1° C. for 15 minutes. Gel permeation chromatography (GPC) analysis shows that the weight average molecular weight (Mw) of the sterilized ferric carboxymaltose is 202 KDa.

Example 2: Preparation of the Ferric Carboxymaltose Solution Using the Oxidized Maltodextrin from Preparation Example 2

Refer to the method of Example 1, except (1) the ferric chloride solution without the addition of hydrochloric acid was used, (2) 17.5 g and 5.6 g of the oxidized maltodextrin solid prepared from Preparation Example 2 were added in batches, and (3) the reaction mixture was further heated to 90 to 95° C. with stirring for 30 minutes after being stirred at 50 to 55° C. for 70 minutes.

The finally purified and isolated intermediate solution, in which the weight average molecular weight of the ferric carboxymaltose is 280 KDa by GPC analysis, was condensed to the concentration of 9.29% and spray dried. 17% ferric carboxymaltose solution prepared therefrom was sterilized. GPC analysis shows that the weight average molecular weight of the sterilized ferric carboxymaltose is 268 KDa.

Example 3: Preparation of the Ferric Carboxymaltose Solution Using the Oxidized Maltodextrin from Preparation Example 1

Refer to the method of Example 1, except (1) an iron chloride solution with 11.414 g of iron content and 7.819 g of 3 N hydrochloric acid were used, and (2) 26.995 g of the oxidized maltodextrin solid prepared from Preparation Example 1 was added totally in a batch.

The finally purified and isolated intermediate solution, in which the weight average molecular weight of the ferric carboxymaltose is 223 KDa by GPC analysis, was condensed to the concentration of 9.21% and spray dried. 17% ferric carboxymaltose solution formulated therefrom was sterilized. GPC analysis shows that the weight average molecular weight of the sterilized ferric carboxymaltose is 205 KDa.

Example 4: Preparation of the Ferric Carboxymaltose Solution Using the Oxidized Maltodextrin from Preparation Example 2

Refer to the method of Example 1, except (1) a ferric chloride solution with 10 g of iron content without the addition of hydrochloric acid was used, and (2) 20 g and 3.1 g of the oxidized maltodextrin solid prepared from Preparation Example 2 were added in batches.

The finally purified and isolated intermediate solution, in which the weight average molecular weight of the ferric carboxymaltose is 247 KDa by GPC analysis, was condensed to the concentration of 9.03% and spray dried. 17% ferric carboxymaltose solution formulated therefrom was sterilized. GPC analysis shows that the weight average molecular weight of the sterilized ferric carboxymaltose is 262 KDa.

Example 5: Preparation of the Ferric Carboxymaltose Solution Using the Oxidized Maltodextrin of Preparation Example 3

Refer to the method of Example 1, except (1) a ferric chloride solution with 20 g of iron content without the addition of hydrochloric acid was used, and (2) 50.2 g and 18 g of the oxidized maltodextrin solid prepared from Preparation Example 3 were added in batches.

The finally purified and isolated intermediate solution, in which the weight average molecular weight of the ferric carboxymaltose is 280 KDa by GPC analysis, was condensed to the concentration of 10.89% and spray dried. 17% ferric carboxymaltose solution prepared therefrom was sterilized. GPC analysis shows that the weight average molecular weight of the sterilized ferric carboxymaltose is 294 KDa.

Example 6: Preparation of the Ferric Carboxymaltose Solution Using the Oxidized Maltodextrin from Preparation Example 4

Refer to the method of Example 1, except (1) a ferric chloride solution with 20 g of iron content without the addition of hydrochloric acid was used, and (2) 50.2 g and 22 g of the oxidized maltodextrin solid prepared from Preparation Example 4 were added in batches.

The finally purified and isolated intermediate solution, in which the weight average molecular weight of the ferric carboxymaltose is 258 KDa by GPC analysis, was condensed to the concentration of 10.36% and spray dried. 17% ferric carboxymaltose solution formulated therefrom was sterilized. GPC analysis shows that the weight average molecular weight of the sterilized ferric carboxymaltose is 296 KDa.

Example 7: Preparation of the Ferric Carboxymaltose Solution Using the Oxidized Maltodextrin from Preparation Example 5

Refer to the method of Example 1, except (1) a ferric chloride solution with 10 g of iron content without the addition of hydrochloric acid was used, and (2) 25.1 g and 20 g of the oxidized maltodextrin solid prepared from Preparation Example 5 were added in batches.

The intermediate solution purified and isolated by ultrafiltration, in which the weight average molecular weight of the ferric carboxymaltose is 308 KDa by GPC analysis, was condensed to the concentration of 10.18% and spray dried. 17% ferric carboxymaltose solution prepared therefrom was sterilized. GPC analysis shows that the weight average molecular weight of the sterilized ferric carboxymaltose is 335 KDa.

Comparative Example 1: Preparation of the Ferric Carboxymaltose Solution According to Example 5 of U.S. Pat. No. 7,612,109B2

A. Preparation of the Oxidized Maltodextrin Solution by Sodium Hypochlorite 21.31 g of maltodextrin was dissolved in 63.93 g of water (dextrose equivalent of 11.63) at 25° C. with stirring, adjusted to pH 10, and oxidized by the addition of 8.29 g of sodium hypochlorite (NaClO) solution (including 13.5% W/W of active chlorine) and 0.1657 g of sodium bromide to give an oxidized maltodextrin solution.

B. Preparation of the Ferric Carboxymaltose Solution

The above oxidized maltodextrin solution and 131.16 g of sodium carbonate solution (17.3% W/W) were added to 83.33 g of stirred iron (III) chloride solution (12% $W_{Fe}$/W) in sequence at room temperature, followed by a sodium hydroxide aqueous solution to adjust pH to 11. Then, the solution was heated to 50° C. with stirring for 30 minutes, adjusted to pH 5 to 6 by the addition of hydrochloric acid, kept at 50° C. with stirring for 30 minutes, further heated to 97 to 98° C. with stirring for 30 minutes, and finally cooled to 25 to 30° C. It was observed that gelation and precipitation occurred.

Comparative Example 2

A. Preparation of the Oxidized Maltodextrin Solid by Hydrogen Peroxide 15 g of maltodextrin was dissolved in 45 mL of water with stirring for 45 minutes at 20 to 25° C. Next, 3.886 g of 50% hydrogen peroxide aqueous solution and 1.524 g of 30% sodium hydroxide aqueous solution were added to the previous solution at 20 to 25° C. and stirred at the same temperature for 2 hours. The reaction mixture was adjusted to pH 3 at 20 to 25° C. by the addition of 3 N hydrochloric acid aqueous solution, slowly added to 474 g of methanol, and stirred at the same temperature for 45 minutes. The precipitated solid was filtered out and dried to give the oxidized maltodextrin solid.

The yield of the oxidized maltodextrin solid is 10.66 g, and the measured value of the dextrose equivalent (DE) is 5.7.

B. Preparation of the Ferric Carboxymaltose Solution

Refer to the method of Example 1, except (1) a ferric chloride solution with 2 g of iron content and 1.37 g of 3 N hydrochloric acid were used, and (2) 5.02 g and 1.24 g of the oxidized maltodextrin solid produced in step A were added in batches. Finally, the reaction mixture was stirred at 50 to 55° C. for 70 minutes, and then cooled to 25 to 30° C. It was observed that gelation and precipitation occurred.

Comparative Example 3

A. Preparation of the Oxidized Maltodextrin Solid by Sodium Hypochlorite

Referring to Example 5 of U.S. Pat. No. 7,612,109B2, 100 g of maltodextrin (with dextrose equivalent of 11.63) was used to give an oxidized maltodextrin solution. The oxidized maltodextrin solution was slowly added to 1,264 g of methanol at 0 to 10° C. and stirred at the same temperature for 45 minutes. The precipitated solid was filtered out and dried to give the oxidized maltodextrin solid.

The yield of the oxidized maltodextrin solid is 86.8 g, and the measured value of dextrose equivalent (DE) is 4.3.

B. Preparation of the Ferric Carboxymaltose Solution

According to the method of Example 1, ultrafiltration was performed for purification and isolation to give an intermediate solution. GPC analysis shows that weight average molecular weight of the ferric carboxymaltose in the intermediate solution is 263 KDa. The intermediate solution was condensed to the concentration of 9.86% and spray dried. 17% ferric carboxymaltose solution was prepared therefrom and sterilized. GPC analysis shows that weight average molecular weight of the sterilized ferric carboxymaltose is 377 KDa.

The experimental data of the aforesaid Examples 1 to 7 and Comparative Examples 1 to 3 are shown in Table 1 below.

TABLE 1

|  | DE of the oxidized maltodextrin solid | Appearance of the FCM solution | Mw (KDa) of the FCM after ultrafiltration | Mw (KDa) of the FCM after sterilization | Percentage change (%) in Mw before/after sterilization |
| --- | --- | --- | --- | --- | --- |
| Example 1 | 1~2 | X | 208 | 202 | 3% |
| Example 2 | <1 | X | 280 | 268 | 7% |
| Example 3 | 1~2 | X | 223 | 205 | 8% |
| Example 4 | <1 | X | 247 | 262 | 6% |
| Example 5 | 2~3 | X | 280 | 294 | 5% |
| Example 6 | 2~3 | X | 258 | 296 | 15% |
| Example 7 | 3~4 | X | 308 | 335 | 9% |
| Comparative Example 1 | N/A* | ○ | N/A | N/A | N/A |
| Comparative Example 2 | 5~6 | ○ | N/A | N/A | N/A |
| Comparative Example 3 | 4~5 | X | 263 | 377 | 43% |

FCM indicates ferric carboxymaltose; Mw means the weight average molecular weight
*Product is an oxidized maltodextrin solution, not the oxidized maltodextrin solid.
X means that no precipitation and no gelation were observed; ○ means that precipitation and gelation were observed.

According to the results of Examples 1 to 7 and Comparative Examples 1 to 3, it shows that the use of the oxidized maltodextrin solid having DE<4 prevents the ferric carboxymaltose solution of the present disclosure from precipitation or gelation, for example, 1<DE<4 in Examples 1, 3, and 5 to 7, and DE<1 in Examples 2 and 4. After sterilization of the ferric carboxymaltose, the percentage change in the molecular weight is as low as 15% or less. As a result, the method of the present disclosure can give the ferric carboxymaltose with high stability. In contrast, referring to Comparative Example 1 of the prior art, the oxidized maltodextrin with undetermined or uncontrolled DE was directly used in the subsequent reaction, resulting in the occurrence of gelation and precipitation in the final produced ferric carboxymaltose solution. In Comparative Examples 2 and 3, the dextrose equivalents (DEs) of the oxidized maltodextrin prepared through different oxidizing agents both are greater than 4. Thereby, the final ferric carboxymaltose solution either incurs precipitation or gelation as shown in Comparative Example 2, or exhibits more than 40% change in the molecular weight after sterilization as shown in Comparative Example 3. These ferric carboxymaltose solutions of the comparative examples clearly show an unstable condition, are not conducive to industrial applications, and further highlight the advantages of the present disclosure in which the oxidized maltodextrin solid having the dextrose equivalent of less than 4 is used.

Test Example 1: Stability Test of the Sterile Ferric Carboxymaltose Solution

The sterilized ferric carboxymaltose solutions prepared from Examples 1 to 6 were stored at 40° C. or at 25 to 30° C. The appearance and the molecular weight of the solutions were analyzed for 4 weeks. The results are shown in Tables 2 and 3 below.

TABLE 2

Storage at 40° C.

| Week | | 0 | 1 | 2 | 3 | 4 |
|---|---|---|---|---|---|---|
| Example 1 | Appearance | X | X | X | X | X |
| | Mw | 202 | 211 | 203 | 207 | 206 |
| | Percentage change | 0% | 4% | 0% | 2% | 2% |
| Example 2 | Appearance | X | X | X | X | X |
| | Mw | 268 | 276 | 280 | 284 | 286 |
| | Percentage change | 0% | 3% | 4% | 6% | 7% |
| Example 3 | Appearance | X | X | X | X | X |
| | Mw | 205 | 208 | 208 | 213 | 205 |
| | Percentage change | 0% | 1% | 1% | 4% | 0% |
| Example 4 | Appearance | X | X | X | X | X |
| | Mw | 262 | 274 | 268 | 275 | 274 |
| | Percentage change | 0% | 5% | 2% | 5% | 5% |
| Example 5 | Appearance | X | X | X | X | — |
| | Mw | 294 | 294 | 297 | 302 | — |
| | Percentage change | 0% | 0% | 1% | 3% | — |
| Example 6 | Appearance | X | X | X | X | — |
| | Mw | 296 | 295 | 300 | 305 | — |
| | Percentage change | 0% | 0% | 1% | 3% | — |

X means that no precipitation and no gelation were observed; the unit of Mw is KDa; and the percentage change refers to the Mw change in percent.
— indicates that it is not detected.

TABLE 3

Storage at 25 to 30° C.

| Week | | 0 | 1 | 2 | 3 | 4 |
|---|---|---|---|---|---|---|
| Example 1 | Appearance | X | X | X | X | X |
| | Mw | 202 | 210 | 204 | 208 | 208 |
| | Percentage change | 0% | 4% | 1% | 3% | 3% |
| Example 2 | Appearance | X | X | X | X | X |
| | Mw | 268 | 272 | 277 | 280 | 282 |
| | Percentage change | 0% | 2% | 3% | 4% | 5% |
| Example 3 | Appearance | X | X | X | X | X |
| | Mw | 205 | 209 | 209 | 214 | 207 |
| | Percentage change | 0% | 2% | 2% | 4% | 1% |
| Example 4 | Appearance | X | X | X | X | X |
| | Mw | 262 | 271 | 266 | 271 | 273 |
| | Percentage change | 0% | 3% | 2% | 3% | 4% |
| Example 5 | Appearance | X | X | X | X | — |
| | Mw | 294 | 294 | 299 | 302 | — |
| | Percentage change | 0% | 0% | 2% | 3% | — |
| Example 6 | Appearance | X | X | X | X | — |
| | Mw | 296 | 295 | 299 | 303 | — |
| | Percentage change | 0% | 0% | 1% | 2% | — |

X means that no precipitation and no gelation were observed; the unit of Mw is KDa; and the percentage change refers to the Mw change in percent.
— indicates that it is not detected.

Test Example 2: Stability Test of the Intermediate Solution

The intermediate solutions (including ferric carboxymaltose) purified and isolated by ultrafiltration in Examples 1, 2, and 4 to 6 were stored at 25 to 30° C. The appearance and the molecular weight of the solutions were analyzed for 2 weeks. The results are shown in Table 4 below.

TABLE 4

| Week | | 0 | 1 | 2 |
|---|---|---|---|---|
| Example 1 | Appearance | X | X | X |
| | Mw | 208 | 212 | 214 |
| | Percentage change | 0% | 2% | 3% |
| Example 2 | Appearance | X | X | X |
| | Mw | 280 | 274 | 276 |
| | Percentage change | 0% | 2% | 1% |

TABLE 4-continued

| Week | | 0 | 1 | 2 |
|---|---|---|---|---|
| Example 4 | Appearance | X | X | X |
| | Mw | 247 | 254 | 260 |
| | Percentage change | 0% | 3% | 5% |
| Example 5 | Appearance | X | X | X |
| | Mw | 280 | 288 | 306 |
| | Percentage change | 0% | 3% | 9% |
| Example 6 | Appearance | X | X | X |
| | Mw | 258 | 294 | 316 |
| | Percentage change | 0% | 14% | 22% |

X means that no precipitation and no gelation were observed; the unit of Mw is KDa; and the percentage change refers to the Mw change in percent.

Analytical Method

Dextrose Equivalent Determination: Fehling's Reagent Determination Method

TS A solution, TS B solution, TS indicator, and sample solution were prepared, respectively, as follows:

TS A solution: dissolving about 34 g of cupric sulfate in 500 mL of deionized water TS B solution: dissolving about 173 g of potassium sodium tartrate and 50 g of sodium hydroxide in 500 mL of deionized water TS indicator: dissolving about 1 mg of methylene blue in 100 mL of deionized water Sample solution: dissolving and diluting about 5 g of a sample to 100 mL with deionized water 5 mL of TS A solution and 5 mL of TS B solution were added in a 125 mL Erlenmeyer flask, heated to boiling, and kept for 2 minutes. The sample solution was added about 0.5 mL before the end of the titration, heated again to boiling, and retained for 2 minutes. Two drops of TS indicator were added. Titration with Sample solution is conducted until the blue color of the liquid disappears. The dextrose equivalent of the sample was calculated through the titration amount.

GPC Determination

The GPC determination was conducted in accordance with the determination of molecular weight and molecular weight distribution of polysaccharides (Chinese Pharmacopoeia 2000 Edition, two parts, Appendix V H). Agilent HPLC 1260 (HPLC-RID) with the Shodex SB-804 HQ column, 8.0×300 mm, was used.

What is claimed is:

1. A method of preparing ferric carboxymaltose with weight average molecular weight between 100,000 and 400,000, the method comprising:
   reacting an aqueous solution containing maltodextrin having the dextrose equivalent of 8 to 15 with an oxidizing agent to obtain an oxidized maltodextrin solid, and
   reacting the oxidized maltodextrin solid with an iron (III) salt solution in acidic and basic conditions in sequence to obtain the ferric carboxymaltose,
   wherein the oxidized maltodextrin solid has a dextrose equivalent less than 4,
   further comprising after the reacting of the aqueous solution containing the maltodextrin and the oxidizing agent, using an organic solvent to precipitate the oxidized maltodextrin solid.

2. The method of claim 1, wherein the oxidizing agent is a combination of hypochlorite and bromide, and the aqueous solution containing maltodextrin and the oxidizing agent are reacted under a basic condition.

3. The method of claim 1, wherein the oxidizing agent is a combination of hydrogen peroxide and chlorite, and the aqueous solution containing maltodextrin and the oxidizing agent are reacted under an acidic condition.

4. The method of claim 1, wherein the oxidized maltodextrin solid is added to the reaction at one time or in batches.

5. The method of claim 4, wherein the oxidized maltodextrin solid is added before reacting under the basic condition.

6. The method of claim 1, further comprising adjusting the reaction to an acidic condition after reacting under the basic condition.

7. The method of claim 1, further comprising purifying and separating the obtained ferric carboxymaltose with an ultrafiltration membrane.

8. The method of claim 7, further comprising treating the obtained ferric carboxymaltose by spray drying to obtain the ferric carboxymaltose solid.

9. The method of claim 8, further comprising dissolving the ferric carboxymaltose solid in pure water to prepare a solution and sterilizing.

* * * * *